United States Patent [19]
Don Michael

[11] Patent Number: 5,339,808
[45] Date of Patent: Aug. 23, 1994

[54] ENDOTRACHEAL-ESOPHAGEAL INTUBATION DEVICES

[76] Inventor: T. Anthony Don Michael, 309 Panorama Dr., Bakersfield, Calif. 93305

[21] Appl. No.: 878,492

[22] Filed: May 5, 1992

Related U.S. Application Data

[63] Continuation-in-part of Ser. No. 679,197, Apr. 2, 1991, abandoned.

[51] Int. Cl.⁵ .............. A61M 16/00; A61M 29/00; A62B 9/02; A62B 9/06
[52] U.S. Cl. .............. 128/207.15; 128/207.16; 128/207.17; 128/911; 128/912; 128/200.26; 604/102
[58] Field of Search .............. 128/200.26, 205.25, 128/207.14, 207.15, 207.16, 207.17, 206.15, 206.24, 206.26, 206.27, 911, 912, DIG. 26; 604/26, 33, 96, 102, 158, 164, 264

[56] References Cited

U.S. PATENT DOCUMENTS

| | | | |
|---|---|---|---|
| 3,874,377 | 4/1975 | Davidson | 128/207.15 |
| 4,090,518 | 5/1978 | Elam | 128/207.15 |
| 4,327,720 | 5/1982 | Bronson et al. | 128/911 |
| 4,497,318 | 2/1985 | Donmichael | 128/207.15 |
| 5,256,099 | 3/1981 | Dryden | 128/200.26 |

*Primary Examiner*—Kimberly L. Asher
*Attorney, Agent, or Firm*—Spensley Horn Jubas & Lubitz

[57] ABSTRACT

Intubation apparatus including an airway device, or main tube, which is to be inserted via the patient's mouth and then into the patient's trachea or esophagus. Components within the main tube are selectively operable for establishing either a first airflow path along the length of the main tube or a second airflow path between the proximal end of the main tube and lateral passages provided in the main tube wall, depending on the location of the main tube. An auxiliary tube is secured to the main tube so that the interior of the auxiliary tube communicates with the interior of the main tube at a location downstream of the lateral passages provided in the main tube wall. A suction tube is insertable through the auxiliary tube and into the main tube to a location beyond the distal end of the main tube.

19 Claims, 5 Drawing Sheets

ENDOTRACHEAL-ESOPHAGEAL INTUBATION DEVICES

CROSS-REFERENCE TO RELATED APPLICATION

The present application is a continuation-in-part of my application Ser. No. 07/679,197, filed Apr. 2, 1991, now abandoned.

BACKGROUND OF THE INVENTION

The present invention relates to intubation devices for use in performing artificial respiration and the like.

Among the devices employed during cardiopulmonary resuscitation (CPR) are various types of airways, including esophageal airways (EOA) and esophageal tracheal combitubes (ETC).

EOAs, one example of which is disclosed in U.S. Pat. No. 4,497,318, must be inserted into the esophagus. If, during insertion, the airway should enter the trachea, it must be withdrawn and reinserted. While, in the hands of a skilled individual, and under normal conditions, such a tube will enter the esophagus, it will initially pass into the trachea in a not insignificant percentage, and perhaps 5–10%, of cases.

In an effort to eliminate the need to insert such a device more than once, various type of ETCs have been proposed. These consist essentially of two tubes disposed side-by-side and having respective air inlets. If the device is inserted into the esophagus, air is blown in via the inlet associated with one tube, whereas if the device initially finds its way into the trachea, air is blown in via the inlet of the other tube. Since each tube must have the cross section required to permit introduction of the required quantity of air, the overall device would, as a rule, have to have at least one relatively large transverse dimension, which makes insertion more difficult and increases possible patient discomfort. In addition, after the device has been inserted, and its location ascertained, time is required to connect the associated air source, such as a bag-valve, to the appropriate tube and care must be taken to verify that connection is being made to the correct tube under emergency conditions. Thus, while ETCs have alleviated certain of the problems associated with the use of such airways, their use nevertheless presents certain complications which will act to delay the start of CPR.

Another device of this type, disclosed in U.S. Pat. No. 3,874,377, employs, in effect, a single tube having an adapter inserted therein for allowing the airway to be utilized whether it has been inserted in the trachea or the esophagus. According to one embodiment disclosed in this patent, the adapter is provided at its distal end with a plug which seals the lumen in the airway, and is further provided with a sleeve which can be moved to selectively open or block passages provided in the region of the proximal end of the airway. When the airway has been inserted to the trachea, the adapter is not inserted, or is removed, and the sleeve is moved into a position in which it blocks the passages located adjacent the proximal end of the airway. Air can then be introduced directly into the patient's lungs. On the other hand, when the airway has been inserted into the patient's esophagus, the adapter is introduced in order to block flow of air directly through the airway and the sleeve is moved to the position in which it opens the passages in the vicinity of the proximal end of the airway, so that air can then be introduced into the patient's lungs.

This embodiment has certain drawbacks. Particularly, it is intended to be initially inserted with the sleeve in the position in which it blocks the passages adjacent the proximal end of the airway and the adapter not inserted. If, in this condition, the airway is inserted into the esophagus, normal flow of air to the patient's lungs will be blocked during the time of insertion of the airway, which can be of some duration, and until it has been determined, by appropriate tests, that the airway is, indeed, in the esophagus and not in the trachea. Thus, during this interval, the patient's condition can be worsened by the airway itself. In addition, in this embodiment, the sleeve can be inadvertently moved from its intended position by contact with interior surfaces in the patient's mouth or throat.

In a second embodiment disclosed in the cited patent, the adapter is secured at the proximal end of the tube, or airway and includes an outer sleeve which may be integral with the airway and an inner sleeve which is rotatable within the outer sleeve between two end positions. In one end position, the distal end of the adapter cooperates with a blocking member disposed at the interior of the airway to close the longitudinal passage which extends through the airway and to open the lateral passages adjacent the proximal end of the airway. In the other end position of the inner sleeve, the lateral passages adjacent the proximal end of the airway are blocked and the longitudinal passage through the airway is opened. Thus, this embodiment also has the drawback that during the time of insertion of the airway, there is always the possibility, regardless of the initial position of the inner sleeve, that the passage to the patient's lungs will be blocked until the actual disposition of the airway within the patient has been determined.

SUMMARY OF THE INVENTION

It is the primary object of the present invention to reduce the time needed to position an airway and commence CPR.

Another object of the invention is to simplify the procedure required to perform CPR with the aid of an airway.

Yet another object of the invention is to minimize the transverse dimensions of such an airway while allowing for adequate air flow.

A further object of the present invention is to avoid the danger of medical complications during intubation of a patient.

Another object of the invention is to provide an intubation apparatus which is characterized by structural simplicity and ease of utilization.

The above and other objects are achieved, according to the invention, by the provision of intubation apparatus comprising:

an airway device composed of a first hollow tube having a wall, a proximal end, a distal end, at least one first opening located in the wall between the proximal and distal ends, and a second opening located in the wall between the first opening and the distal end, the first hollow tube being insertable, via its distal end, into a patient's mouth and into one of the esophagus and trachea of the patient, the first hollow tube providing a first air flow path between the proximal end and the distal end of the first hollow tube and a second air flow path between the proximal end of the first hollow tube and the first opening;

a second hollow tube having a wall, a proximal end and a distal end, the second hollow tube being joined to the first hollow tube so that the distal end of the second hollow tube is aligned with the second opening;

a third tube having a wall, a proximal end and a distal end, the third hollow tube having an outer diameter which is smaller than the inner diameters of each of the first and second hollow tubes and being insertable into the first and second hollow tubes to extend along the second hollow tube and along a portion of the first hollow tube from the second opening in the direction away from the proximal end of the first hollow tube;

air flow directing means comprising first flow control means disposed for closing the first opening to block the second air flow path, and second flow control means disposed for blocking the interior of the first hollow tube to block the first air flow path; and means for operating the air flow directing means for opening the first air flow path when the distal end of the first hollow tube is in the trachea and for opening the second air flow path when the distal end of the first hollow tube is in the esophagus.

Objects according to the invention are further achieved by the provision of intubation apparatus comprising:

a first hollow tube having an imperforate wall, a proximal end and a distal end, the first hollow tube being insertable, via its distal end, into a patient's mouth and into one of the esophagus and trachea of the patient; and a second hollow tube having a wall provided with an opening, a proximal end and a distal end, the distal end of the second hollow tube being secured to the outer surface of the wall of the first hollow tube at a location such that when the first hollow tube is inserted into the esophagus of the patient, the opening in the wall of the second hollow tube is in fluid flow communication with the patient's trachea, the second hollow tube being open at its proximal end and being of a length such that when the first hollow tube is properly inserted into a patient, the proximal end of the second hollow tube will extend out of the patient's mouth.

DESCRIPTION OF THE PREFERRED EMBODIMENTS

Figure 1A:
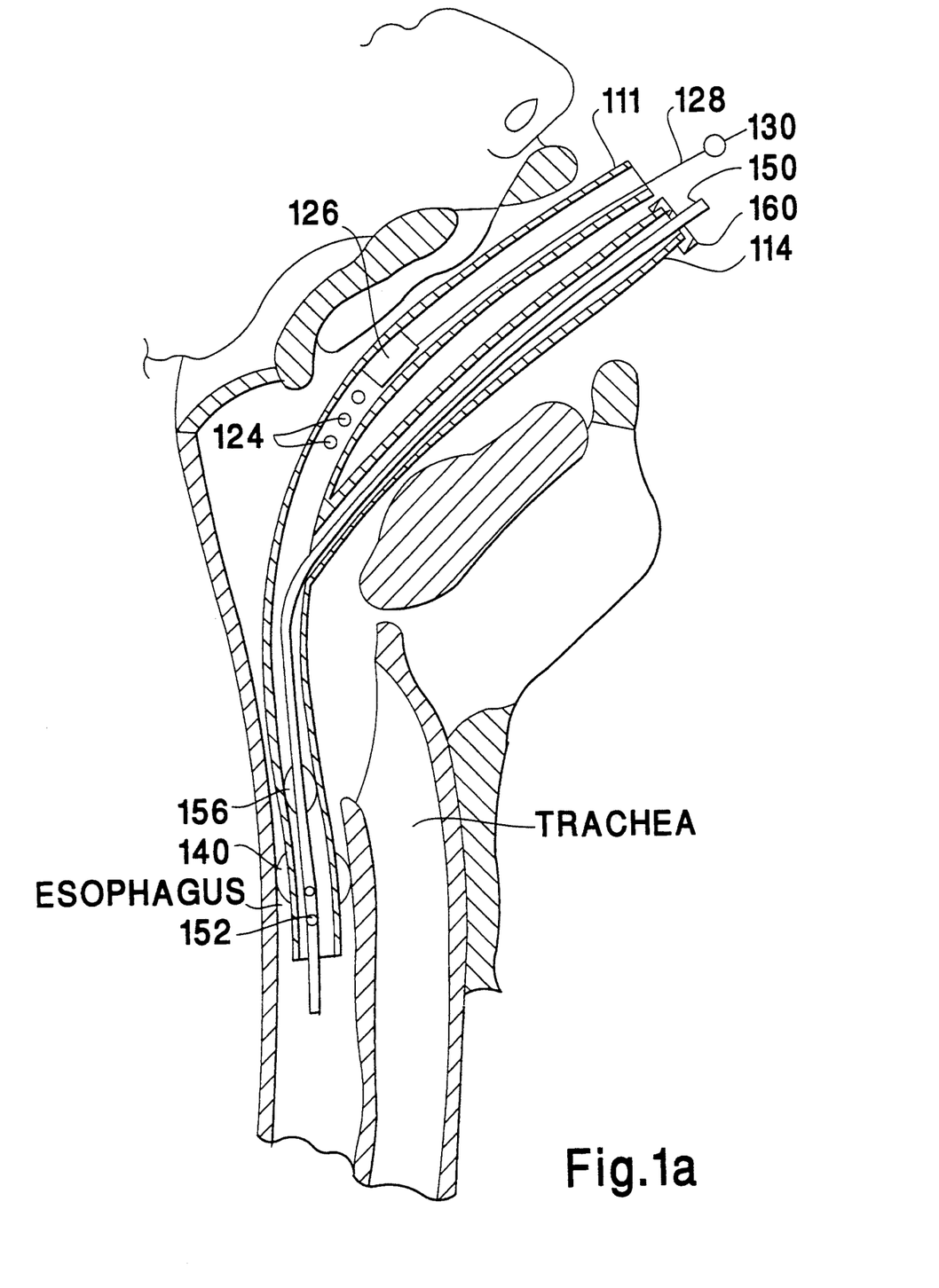
FIGS. 1a and 1b are cross-sectional views of an intubation device according to a preferred embodiment of the invention inserted into the esophagus and trachea, respectively.
Figure 1B:
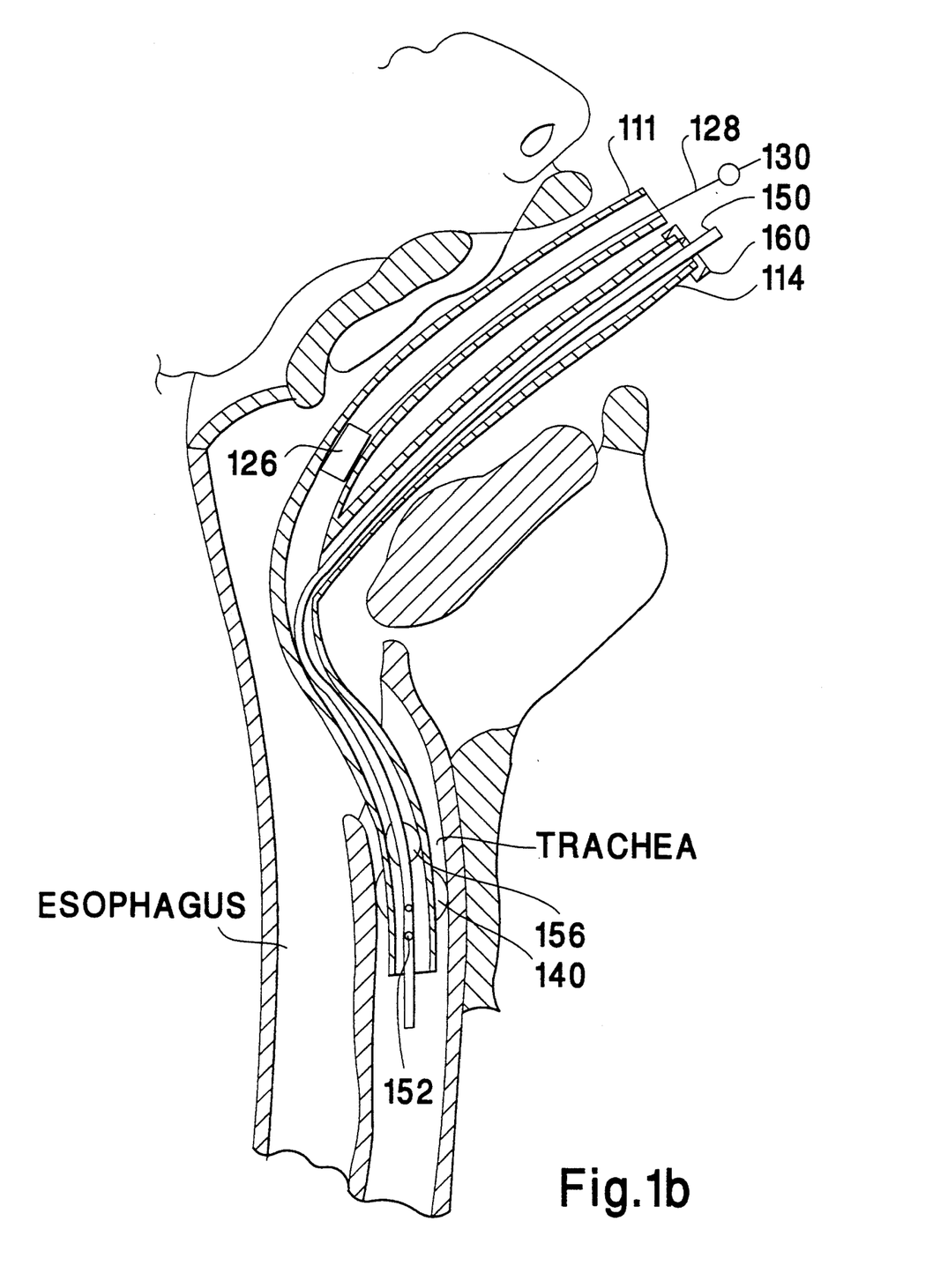

An advantageous embodiment of the invention is illustrated in FIGS. 1a and 1b, this embodiment being a multifunction endoesotube which can be used to insufflate the lungs, whether placed in the esophagus or trachea and which can also be employed to suction fluids from either the lungs or the stomach, depending on the passage into which it has been inserted, and to enable drugs, including antidotes, or other liquids, to be introduced into the lungs, if the device has been inserted into the trachea, or into the stomach if the device has been inserted into the esophagus.

A device according to this embodiment includes a main airway tube 111 which is open at both ends to provide a longitudinal air passage that extends along its entire length, and an auxiliary tube 114 which is also open at both ends to provide a longitudinal passage that extends along its entire length. The side wall of tube 111 is provided with an opening in which is connected the open distal end of tube 114. Tube 114 is substantially shorter than tube 111 and both tubes have proximal ends which will extend out of the patient's mouth when the device has been fully inserted.

Tube 111 is provided with an array of openings 124 via which fluid, such as air or oxygen, can flow between the interior of, and the region, surrounding tube 111. Openings 124 may be located only on a portion of the circumference of tube 111 in a manner such that openings 124 will not be present at the side of tube 111 which is directed toward the patient's tongue.

Within tube 111 there is disposed an annular sleeve 126 which is slidable in the longitudinal direction of tube 111. Sleeve 126 is connected via a stiff wire 128 to a handle 130 which can be manipulated to move sleeve 126 between the position shown in FIG. 1a, in which openings 124 are unobstructed and the position shown in FIG. 1b in which sleeve 126 covers openings 124 in order to prevent the flow of fluid through those openings.

Tube 111 carries an inflatable balloon or cuff 140 which extends circumferentially around the outer surface of tube 111, adjacent the distal end thereof. The interior of balloon or cuff 140 is connected to a source of inflation fluid via a small diameter tube, or lumen, which extends along main airway tube 111, in a manner similar to that described in copending application Ser. No. 07/679,197. Preferably, balloon 140 is a high compliance, low pressure balloon.

Auxiliary tube 114 is provided for introduction of a small diameter tube 150 which is open at both ends and presents a longitudinal through passage extending along its entire length. Tube 150 has an outer diameter which is smaller than the inner diameters of tubes 111 and 114. At a short distance from its distal end, tube 150 is provided with a plurality of openings 152 which extend through the tube wall. Tube 150 is of a length sufficient to permit its distal end to extend beyond the distal end of tube 111. The proximal end of tube 150 may be adapted for connection to suction apparatus (not shown).

Associated with tube 150 is an inflatable balloon or cuff 156 which may be either structurally separate from tube 150, i.e. carried by a separate tube, or may be mounted on the outer wall of tube 150. A small diameter inflation tube, or lumen, (not shown) is connected to balloon 156 and may be mounted on the wall of tube 150, or may be independent therefrom. This lumen may also be arranged as described in copending application Ser. No. 07/679,197.

Figure 1C:
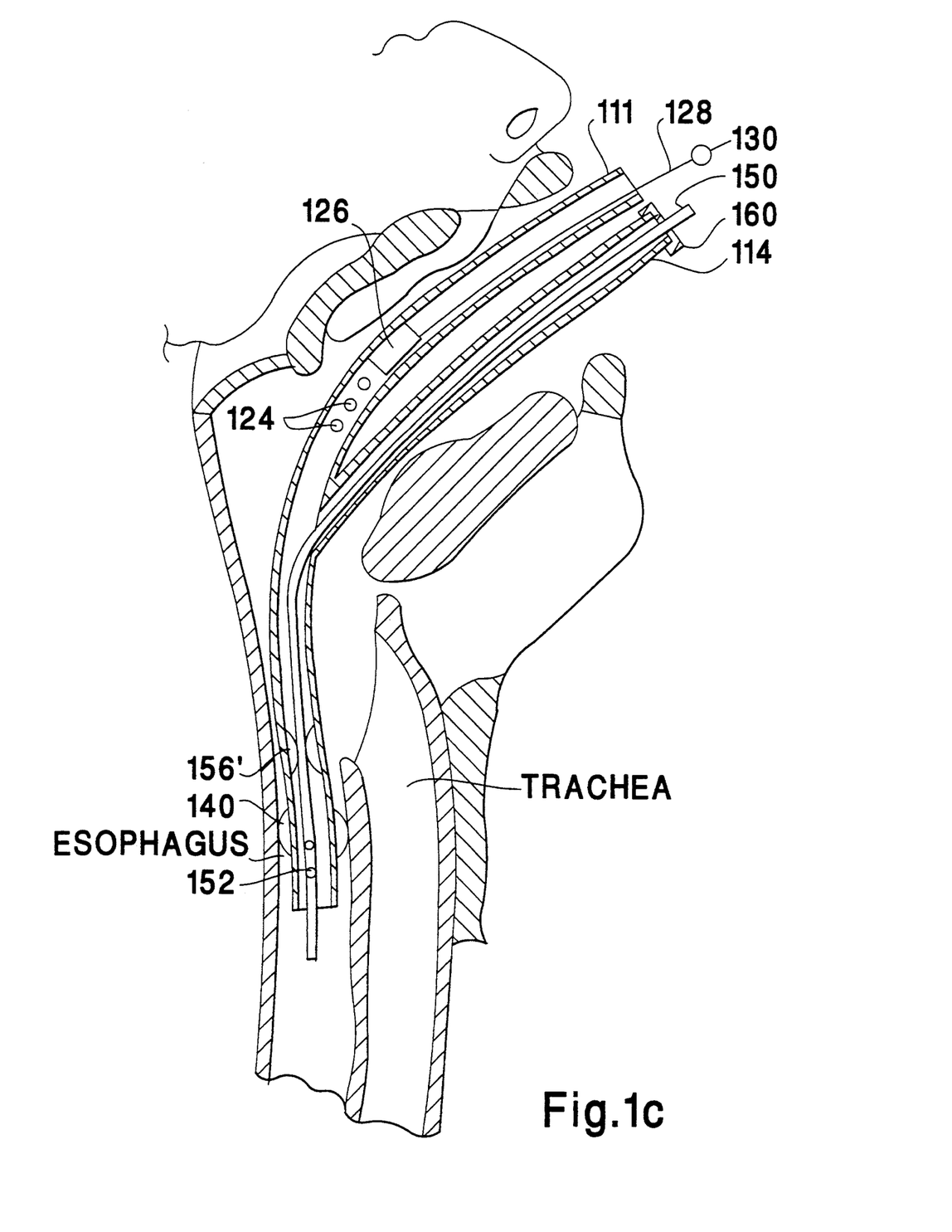
FIG. 1c is a view similar to FIGS. 1a and 1b showing a modified form of the device inserted into the esophagus.

If desired, balloon 156 can be replaced by an annular cuff, or balloon, 156' mounted on the interior wall surface of tube 111, as shown in FIG. 1c. Such cuff, or balloon 156', would be deflated whenever it is desired to insert tube 150 into the distal portion of main airway tube 111.

Each lumen for inflating a respective balloon can be provided with a one-way valve which normally permits the passage of air or other inflating gas only in the inflating direction and which can be opened to permit balloon deflation by insertion of a syringe.

In further accordance with the invention, if tube 150 is to be installed only in the event tube 111 has entered the esophagus, balloon 156 or 156' can be replaced by a sealing plug made, for example, of foam rubber, mounted on tube 150.

In order to utilize the device illustrated in FIGS. 1a and 1b, the proximal end of tube 111, which proximal end may be tapered or rounded if desired, and may be lubricated, is inserted along the patient's tongue and against the posterior pharyngeal wall. Insertion of tube 111 continues until its distal end is properly positioned. Typically, this is a position in which the distal end of tube 111 is approximately 13.8 inches (35 cm) from the patient's mouth opening. During this portion of a procedure, tube 111 need not be initially assembled with a mask, to be described below.

The proper position of the distal end of tube 111 within the patient can be verified by providing tube 111, at a small distance from its proximal end, with a first reference mark which will have a defined location relative to the patient's mouth when tube 111 has been inserted by the requisite amount. During insertion, balloon 140 is deflated.

Tube 150 may be introduced into main airway tube 111, via auxiliary tube 114, either prior to or after insertion of the device into the patient. Then, with balloon 156 deflated, as shown in FIG. 1b, tube 150 is moved along the interior of tube 111 so that the distal end of tube 150 traverses the lower portion of tube 111 while a suction force is applied, via the proximal end of tube 150, in order to withdraw from the interior of tube 111 any fluids which have accumulated therein during insertion. Openings 152 aid in the performance of this suctioning procedure.

As is known, at this time, the distal end of tube 111 may be in the patient's esophagus, leading to the stomach as shown in FIGS. 1a and 1c, or in the patient's trachea, leading to the lungs, as shown in FIG. 1b. As a general rule, even skilled personnel cannot consistently direct such a tube into a selected one of these passages.

According to the present invention, the precise location of tube 111 is determined by delivering air through tube 150, via the proximal end thereof, while using a stethoscope to listen for signs of air flowing into the stomach and visually observing the patient's chest for signs of lung inflation. During this time, since air is being introduced via tube 150, openings 124 may be unblocked so that the normal flow of air to and from the patient's lungs is unobstructed regardless of the location of tube 111.

If the above-described tests indicate that tube 111 is in the trachea, sleeve 126 is moved to the position in which it blocks openings 124, tube 111 may be pulled back to a point at which its distal end is approximately 24 cm from the patient's mouth opening, again aided by a second reference mark on tube 111 which will be visible when tube 111 has been retracted by the proper amount, and balloon 140 is inflated by an amount appropriate to tracheal insertion, in order to seal the annular region between tube 111 and the trachea. The attending medical personnel can then proceed to force air through tube 111 and into the patient's lungs. In this event, a mask is not required.

If, on the other hand, the various observations reveal that tube 111 is in the esophagus, sleeve 126 is maintained at, or moved to, the position in which openings 124 are unobstructed and balloon 156 is inflated to block the air passage through tube 111 downstream of openings 124. If balloon 156 is carried by tube 150, this requires that tube 150 be inserted into tube 111 to bring balloon 156 to a suitable location. A mask, to be described below, is then coupled to the proximal end of tube 111 and balloon 140 is inflated by an amount appropriate for esophageal insertion. During this time, a suction force can be applied to tube 150 in order to continue to suction fluids from the patient's esophagus and stomach.

In addition, during either mode of use of the device, suction tube 150 can be employed to administer an appropriate medication, either to the lungs in the case of tracheal insertion or the stomach in the case of esophageal insertion.

Whether the device employs balloon 156 carried by tube 150, as shown FIGS. 1a and 1b, or balloon 156' mounted on the interior wall of tube 111, as shown in FIG. 1c the inflated condition of the balloon can be verified by applying a longitudinal force to tube 150 and observing its resistance to movement.

When air is being blown into the patient's lungs, the proximal end of tube 114 may be closed by a suitable cap 160 which fits around tube 150.

Figure 2:
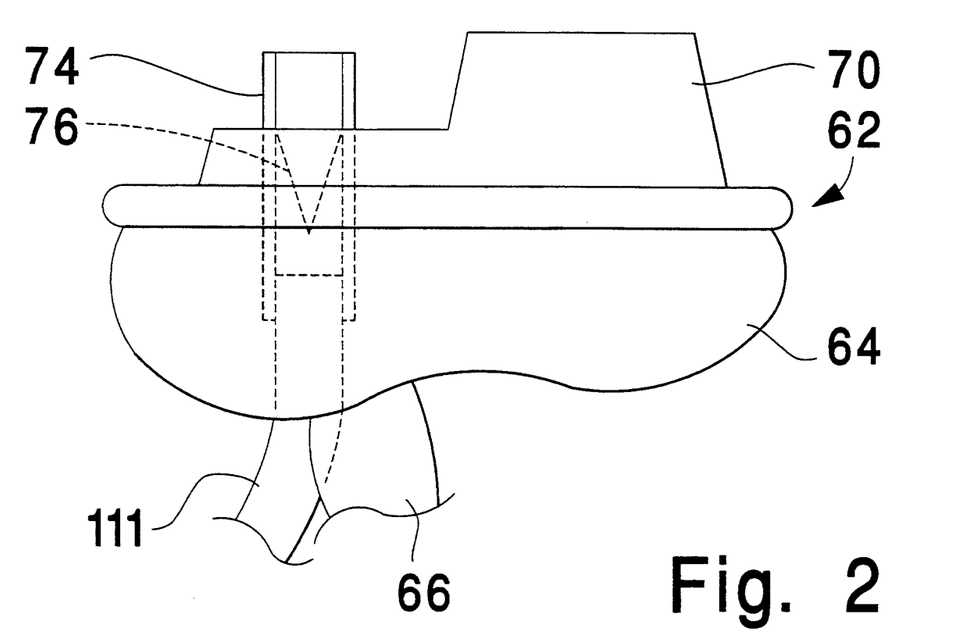
FIG. 2 is a side elevational view of a mask according to the invention for use with the device of FIG. 1.

As noted above, when tube 111 is found to have been inserted into the esophagus, the proximal end of tube 111 is to be connected to a mask which covers the patient's mouth, and portions of the face surrounding the mouth. One embodiment of a mask according to the present invention is illustrated in FIG. 2. This mask may have a physical appearance similar to that of the mask illustrated in U.S. Pat. No. 4,497,318. However, mask 62 differs from the mask shown in that patent in certain significant respects, as will be described in detail below. Thus, in place of the inflatable collar disclosed in that patent, mask 62 according to the present invention is provided with a collar 64 which may be constituted by a molded plastic piece or a foam pad which is not constructed to be inflated. When collar 62 is made of a suitably configured molded plastic or foam pad, it can be made to conform satisfactorily to the patient's face, while the undesirable additional step of inflating the collar is avoided. As a further alternative, collar 64 may be constituted by a thin sheet of flexible material, such as a silicone rubber.

In further accordance with the invention, collar 64 is provided with a strap arrangement 66 which extends around to the other side of collar 64 (not visible in FIG. 2) and is used to secure mask 62 to the patient's face, with collar 64 properly positioned, so that the resuscitation procedure can be performed while the attention of the attending medical personnel need not be diverted to verify that the mask is in place. Mask 62 further includes a cup-shaped section 70 which will fit over the patient's nose when mask 62 is in place, along with a tube 74 which is to be coupled to, and form an extension of, tube 111, and a further port (not shown) for passage of auxiliary tube 114.

As can be seen in FIG. 2, the lower, or distal, end of tube 74 is flared to facilitate coupling with the proximal end of tube 111.

Tube 74 is given a free length, for example of the order of at least three inches (7.6 cm), and preferably at least four inches (10.1 cm), in order to facilitate access either by the mouth of an individual who will perform resuscitation or by a source of air or oxygen.

In further accordance with the invention, tube 74 is equipped with a one-way valve 76 which permits air to be blown into the patient's lungs via tube 74, but prevents the flow of air or body fluids upwardly from the patient and through the proximal end of tube 74, to thereby protect operating personnel who are performing resuscitation by mouth against contamination by viruses or other harmful organisms. Valve 76 can have a form similar to that of the one-way valve disclosed in U.S. Pat. No. 4,998,530.

Reverting again to FIG. 1a, when, during resuscitation, tube 111 is located in the patient's esophagus, air can be expelled from the patient's lungs around tube 111 and then between collar 64 and the patient's face so that the mask need not be removed to permit the patient to exhale.

The provision of tube 114, which provides a passage for insertion of suction tube 150, offers the advantage of facilitating manipulation of tube 150 and connection of that tube to either a suction source or a medication supply source, while the proximal region of tube 111 is continuously accessible for resuscitation purposes.

Figure 3:
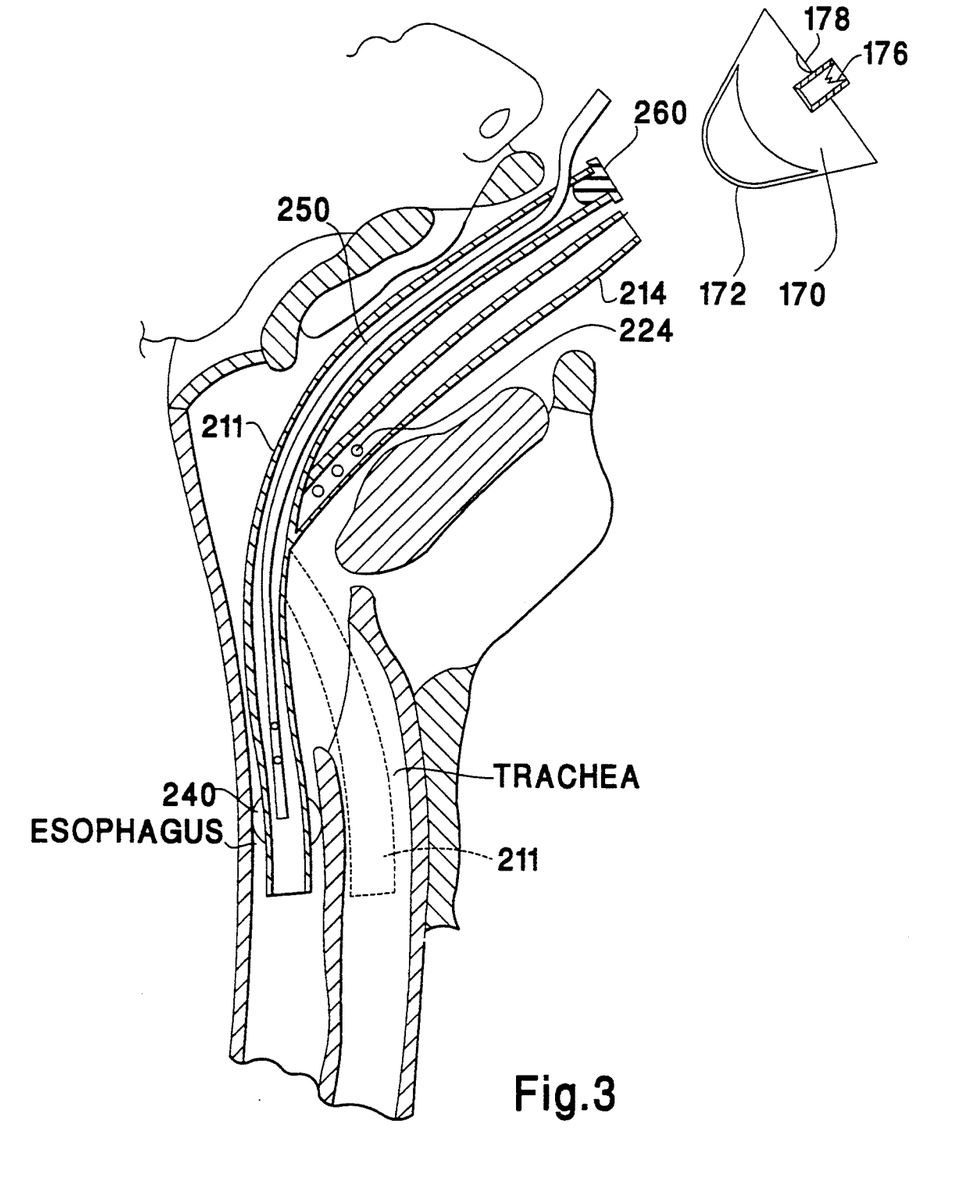
FIG. 3 is a view, in cross section, of a further embodiment of a device according to the invention, including an airway and a mask which is detachably securable to the airway.

A further embodiment of the invention, composed of an airway and a detachable mask, is illustrated in FIG. 3, which shows an airway and mask in cross section.

According to this embodiment, there is provided a main airway tube 211 composed of a sidewall which is completely free of perforations and which is open at both ends to define a longitudinal air passage. Joined to tube 211, at a location which is centered at a point approximately 2 inches (5 cm) from the proximal, or upper, end of tube 211, is the distal end of an auxiliary tube 214 which is open at its proximal end and which has a sidewall provided with a plurality of openings 224 defining lateral air passages. Thus, the distal end of tube 214 is closed by the sidewall of tube 211. An inflatable annular cuff 240 is secured to the outer wall of tube 211, in the vicinity of the distal end thereof. Cuff 240 performs the same function as cuff 140 of FIGS. 1a–1c and may be inflated in the same manner as the cuff 140 of FIGS. 1a–1c.

A tube 250 is introduced into tube 211, preferably via an opening provided in the wall of tube 211 at a location adjacent the proximal end thereof. Tube 250 has an outer diameter which is smaller than the inner diameter of tube 211. Tube 250 is movable longitudinally within tube 211 and is provided to perform functions similar to those described above with respect to tube 150 of FIGS. 1a–1c. Tube 250 may be provided with lateral openings at a location corresponding to the location of openings 152 in tube 150 of FIGS. 1a–1c and tube 250 is preferably given a length sufficient to allow its distal end to extend beyond the distal end of tube 211 in order to enter the patient's stomach or lungs.

The airway device shown in FIG. 3 may be inserted into a patient in the manner described above with respect to the embodiment of FIGS. 1a–1c, and its location, whether in the esophagus or trachea, will be determined also in the manner described with reference to the embodiment of FIGS. 1a–1c.

In this embodiment, if main tube 2 11 is found to have been inserted into the trachea, as shown in broken lines in FIG. 3, resuscitation can be performed immediately via the proximal end of tube 211, after suitable inflation of cuff 240, and in this case tube 214 will perform no function.

On the other hand, if it is determined that tube 211 has been inserted into the esophagus, air may then be introduced into the lungs directly via tube 214. In this case, cuff 240 will also be inflated, and the proximal end of tube 211 may be blocked by a plug 260 to prevent the expulsion of stomach fluids. The tube assembly will at this time be properly located to assure that air flowing via openings 224 will be delivered to the patient's lungs.

When tube 211 is located in the esophagus, so that resuscitation is performed via auxiliary tube 214, it is preferred that the patient's face be covered with a mask, as described above with respect to FIGS. 1a–1c and 2. In the case of the embodiment shown in FIG. 3, the mask is composed of a thin sheet 170 of flexible material, for example of silicone rubber, having two straps 172 intended to be fitted around the victim's ears in order to hold the mask in place. Sheet 170 and straps 172 may be constructed in the manner disclosed in U.S. Pat. No. 4,998,530. Sheet 170 carries an extension tube 174 containing a one-way valve 176, these components corresponding in structure to tube 74 and valve 76 illustrated in FIG. 2. Tube 174 may be coupled to the proximal end of tube 214 in the manner described above with reference to FIG. 2 relative to the coupling of tube 111. Sheet 170 may additionally be provided with an opening 178 for access to plug 260. When the mask is assembled to the airway device, the proximal end of tube 250 can project beyond sheet 170 to permit the performance of suction procedures and/or the administration of medication to the victim's stomach.

A significant advantage of the embodiment shown in FIG. 3 is its extreme structural simplicity, and in particular the absence of any movable parts, other than tube 250.

The proximal ends of tubes 211 and 2 14 may be prominently marked, as by color coding and/or suitable labels, to indicate which tube is to be utilized if tube 211 is in the trachea or in the esophagus. In addition, each of tubes 211 and 2 14 may be provided, in the vicinity of its proximal end, with a known sensing disc for providing an indication of end tidal $CO_2$. The indication produced by each such disc can serve to indicate, or confirm, whether tube 211 is in the esophagus or the trachea.

In addition to the elements illustrated, sheet 170 may be provided with a passage for a further suction tube which will pass into the patient's mouth to permit suctioning of fluids therefrom.

As in the operation of the embodiment of FIGS. 1a–1c and 2, when the mask is coupled to tube 214, air expelled from the patient's lungs can flow around tube 214 and tube 174 and then between sheet 170 and the patient's face.

The materials employed to construct embodiments of the invention will be those conventionally used for esophageal and endotracheal intubators. The components of devices according to the invention can be constructed so as to be sterilizable and reusable, or can be constructed so as to be disposable after a single use.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Intubation apparatus comprising:
   an airway device composed of a first hollow tube having an inner diameter, a wall, a proximal end, a distal end, at least one first opening located in said wall between said proximal and distal ends, and a second opening located in said wall between said first opening and said distal end, said first hollow tube being insertable, via its distal end, into a patient's mouth and into one of the esophagus and trachea of a patient, said first hollow tube providing a first air flow path between said proximal end and said distal end of said first hollow tube and a second air flow path between said proximal end of said first hollow tube and said first opening;
   a second hollow tube having an inner diameter, a wall, a proximal end and a distal end, said second hollow tube being joined to said first hollow tube so that said distal end of said second hollow tube is aligned with said second opening;
   a third hollow tube having a wall, a proximal end and a distal end, said third hollow tube having an outer diameter which is smaller than the inner diameters of each of said first and second hollow tubes and being insertable into said first and second hollow tubes to extend along said second hollow tube and along a portion of said first hollow tube from said second opening in the direction away from said proximal end of said first hollow tube;
   air flow directing means comprising first flow control means disposed for closing said first opening to block said second air flow path, and second flow control means disposed for blocking the interior of said first hollow tube to block said first air flow path; and
   means for operating said air flow directing means for opening said first air flow path when said distal end of said first hollow tube is in the trachea and for opening said second air flow path when said distal end of said first hollow tube is in the esophagus.

2. Apparatus as defined in claim 1 wherein said first flow control means comprise a sleeve mounted at the inside of said wall of said first hollow tube and moveable between a first position in which said sleeve blocks said first opening and a second position in which said sleeve does not block said first opening.

3. Apparatus as defined in claim 2 wherein said means for operating comprise a control member extending between said sleeve and a region which will be outside of the patient's mouth when said device is inserted for moving said sleeve in at least one direction between said first and second positions.

4. Apparatus as defined in claim 1 wherein said second flow control means comprise an inflatable blocking element which is inflatable to seal the interior of said first hollow tube while permitting said third hollow tube to extend past said blocking element.

5. Apparatus as defined in claim 4 wherein said inflatable blocking element is carried by said third hollow tube.

6. Apparatus as defined in claim 4 wherein said inflatable blocking element is carried at an interior surface of said wall of said first hollow tube.

7. Apparatus as defined in claim 1 further comprising a mask arranged to be placed on the patient's face and having a hollow member couplable to said proximal end of said first hollow tube.

8. Apparatus as defined in claim 7 wherein said hollow member is dimensioned such that when said mask is on the patient's face, said hollow member projects at least 7.6 cm out of said mask.

9. Apparatus as defined in claim 8 wherein said hollow member projects at least 10.1 cm.

10. Apparatus as defined in claim 7 wherein said mask further comprises a collar disposed to fit around the patient's mouth, said collar being made of a resilient material and being non-inflatable.

11. Apparatus as defined in claim 10 wherein said collar comprises a flexible sheet of silicone rubber and at least one strap fastened to said sheet for securing said mask on the patient's face.

12. Apparatus as defined in claim 7 wherein said mask comprises a strap for securing said mask on the patient's face.

13. Apparatus as defined in claim 7 wherein said mask further comprises a one-way valve mounted in said hollow member for permitting fluid flow through said hollow member only in the direction from said hollow member to said first hollow tube when said first hollow tube is coupled to said hollow member, while preventing the flow of air and airborne materials through said hollow member in a direction from said first tube to said hollow member.

14. Apparatus as defined in claim 1 wherein said third hollow tube is provided with at least one opening in its wall in the vicinity of said distal end of said third hollow tube.

15. Intubation apparatus comprising:
    a first hollow tube having an imperforate wall, a proximal end and a distal end, an inner diameter, an outer diameter, and passage sealing means extending circumferentially about the outer diameter, said first hollow tube being inserted, via its distal end, into a patient's mouth and into one of two positions, a first position wherein said distal end of said first hollow tube is inserted into the esophagus of a patient, and a second position wherein said distal end of said first hollow tube is inserted into the trachea of a patient, in both said first and said second positions, said proximal end of said first hollow tube extending out of the patient's mouth;
    a second hollow tube having an inner diameter, a wall provided with an opening, a proximal end and a distal end, said distal end of said second hollow tube being secured to the outer surface of said wall of said first hollow tube, said distal end of said second hollow tube being closed by said imperforate wall of said first hollow tube, said proximal end of said second hollow tube being open and offset from said proximal end of said first hollow tube, and said proximal end of said second hollow tube in both said first and said second positions of said distal end of said first hollow tube, extending out of the patient's mouth;
    said distal end of said first hollow tube in said first position inserted into the esophagus of a patient, having said proximal end of said second hollow tube comprising the sole means for introducing air into the patient's lungs via air entering said proximal end of said second hollow tube and flowing through said opening in said wall of said second hollow tube, said opening in said wall of said second hollow tube being in fluid flow communication with the patient's trachea; and said distal end of said first hollow tube in said second position inserted into the trachea of a patient, having said passage sealing means preventing airflow between said second hollow tube and the patient's trachea, said proximal end of said first hollow tube comprising the sole means for introducing air into the patient's lungs via air flow entering said proximal end of said first hollow tube, flowing through said inner diameter of said first hollow tube, exiting the distal end of said first hollow tube, and entering the patient's lungs.

16. Apparatus as defined in claim 15 further comprising a third hollow tube having a wall, a proximal end and a distal end, said third hollow tube having an outer diameter which is smaller than the inner diameter of said first hollow tube and being insertable into said first hollow tube to extend along said first hollow tube in the direction away from said proximal end of said first hollow tube to at least the vicinity of said distal end of said first hollow tube.

17. Apparatus as defined in claim 16 further comprising a mask arranged to be placed on the patient's face and having a hollow member couplable to said proximal end of said second hollow tube.

18. Apparatus as defined in claim 17 wherein said mask comprises a flexible sheet dimensioned to cover the patient's face in a region surrounding the patient's mouth and having at least one strap for securing said sheet on the patient's face.

19. Apparatus as defined in claim 17 wherein said mask further comprises a one-way valve mounted in said hollow member for permitting fluid flow through said hollow member only in the direction from said hollow member to said second hollow tube when said second hollow tube is coupled to said hollow member, while preventing the flow of air and airborne materials through said hollow member in a direction from said second hollow tube to said hollow member.

* * * * *